United States Patent
Li et al.

(10) Patent No.: US 12,336,849 B2
(45) Date of Patent: Jun. 24, 2025

(54) SYSTEMS AND METHODS FOR IMPROVED COMPUTED TOMOGRAPHY USING PHOTON-COUNTING DETECTORS

(71) Applicant: Wisconsin Alumni Research Foundation, Madison, WI (US)

(72) Inventors: Ke Li, Madison, WI (US); Guang-Hong Chen, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 363 days.

(21) Appl. No.: 17/970,722

(22) Filed: Oct. 21, 2022

(65) Prior Publication Data
US 2024/0148342 A1 May 9, 2024

(51) Int. Cl.
A61B 6/03 (2006.01)
A61B 6/42 (2024.01)
G01T 1/20 (2006.01)

(52) U.S. Cl.
CPC .............. *A61B 6/03* (2013.01); *A61B 6/4241* (2013.01); *G01T 1/20* (2013.01)

(58) Field of Classification Search
CPC ............ A61B 6/03; A61B 6/4241; G01T 1/20
See application file for complete search history.

(56) References Cited

U.S. PATENT DOCUMENTS

| | | | |
|---|---|---|---|
| 9,977,140 B2* | 5/2018 | Wang | A61B 6/482 |
| 2005/0173641 A1* | 8/2005 | Unger | G01T 1/20181 |
| | | | 348/E5.086 |
| 2010/0204942 A1* | 8/2010 | Danielsson | G01T 1/242 |
| | | | 702/85 |
| 2018/0172849 A1* | 6/2018 | Nelson | G01T 1/20182 |

OTHER PUBLICATIONS

"GE Healthcare Pioneers Photon Counting CT with Prismatic Sensors Acquisition," GE HealthCare, Press Releases, Nov. 20, 2020.

* cited by examiner

*Primary Examiner* — David P Porta
*Assistant Examiner* — Fani Polyzos Boosalis
(74) *Attorney, Agent, or Firm* — Quarles & Brady, LLP (57) ABSTRACT

A system and method for a hybrid detector for a computed tomography (CT) system are provided that include a semiconductor detector arranged to generate photon-counting CT data upon receiving x-rays and a scintillator detector arranged proximate to the semiconductor detector to receive scattered x-rays and generate energy-integrating CT data upon receiving the scattered x-rays.

22 Claims, 10 Drawing Sheets

SYSTEMS AND METHODS FOR IMPROVED COMPUTED TOMOGRAPHY USING PHOTON-COUNTING DETECTORS

CROSS-REFERENCE TO RELATED APPLICATIONS

Not applicable.

STATEMENT REGARDING FEDERALLY SPONSORED RESEARCH

Not applicable.

BACKGROUND

The present disclosure relates to systems and methods for improving computed tomography (CT) systems and, more particularly, to systems and methods of manufacturing and operating a CT detector system that includes a photon counting detector and a scintillator in an integrated system.

In traditional computed tomography systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object and each detector element produces a separate electrical signal that relates to the attenuation of the beam. The linear attenuation coefficient is the parameter that describes how the intensity of the x-rays changes when passing through an object. Often, the "mass attenuation coefficient" is utilized because it factors out the dependence of x-ray attenuations on the density of the material. The attenuation measurements from all the detectors are acquired to produce the transmission map of the object.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two dimensional (2D) scan, data is processed to construct an image that corresponds to a 2D slice taken through the object. The prevailing method for reconstructing an image from 2D data is referred to in the art as the filtered back-projection (FBP) technique. This process converts the attenuation measurements from a scan into integers called "CT numbers" or "Hounsfield units", which are used to control the brightness of a corresponding pixel on a display.

Over the past 15 years, much effort has been committed to lowering radiation dose for x-ray CT imaging due to the potential cancer risks associated with the use of ionizing radiation in CT. Many efforts have been made to develop and commercialize systems and methods that enable low-dose CT imaging. Primarily, this has yielded noise-reduction algorithms that seek to reduce the inevitable decreases in SNR as dose is decreased. However, CT hardware with improved radiation dose efficiency, primarily x-ray detectors such as photon counting detectors, have also been studied and developed to enable low dose CT imaging. Photon counting detector CT (PCD-CT) has been featured as one of the most important advances in low dose CT imaging due to its powerful noise rejection functionality in addition to other advantages such as spectral CT imaging capability. Currently, PCD-CT has been developed by major CT manufacturers for preclinical and, recently clinical evaluations.

At the core of the PCCT technology is a semiconductor-based photon counting detector (PCD) that directly converts the energy of each x-ray photon into mobile electric charges (electrons and holes). Driven under a strong external electric field created by electrode pads coupled to the semiconductor, the motions of those charges induce a voltage pulse with a magnitude proportional to the photon energy imparted. By operating the detector under the pulse mode with multiple voltage comparators, the number of input photons can be counted, and the energies of individual photons can be deduced. This provides the needed information for both conventional attenuation measurements and material decomposition.

Most major commercial CT vendors that have strategically pursued PCCT as their next-generation flagship product have chosen cadmium telluride (CdTe) or its variant, CdZnTe (CZT), as the x-ray sensor material, while some vendors have chosen silicon (Si). As illustrated in Table 1, Si indeed has certain attractive features.

TABLE 1

Material Properties of Si and CdTe

| Material | | Si | CdTe |
|---|---|---|---|
| Charge Mobility $\left(\frac{cm^2}{s \cdot V}\right)$ (at room temperature typical doping level) | electrons | 1400 | 1100 |
| | holes | 480 | 100 |
| Charge Lifetime (μs) (at room temperature, typical doping level) | electrons | >700 | 2.7 |
| | holes | >700 | 30 |
| Atomic number | | 14 | 50 |
| Density (g/ml) | | 2.3 | 6.2 |

Figure 1A:
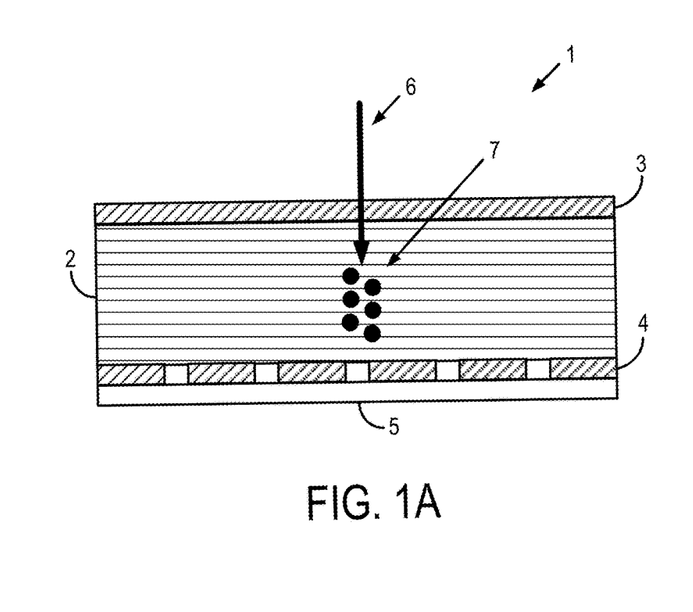
FIG. 1A is a schematic diagram of one, traditional photon counting PC) detector.
Figure 1B:
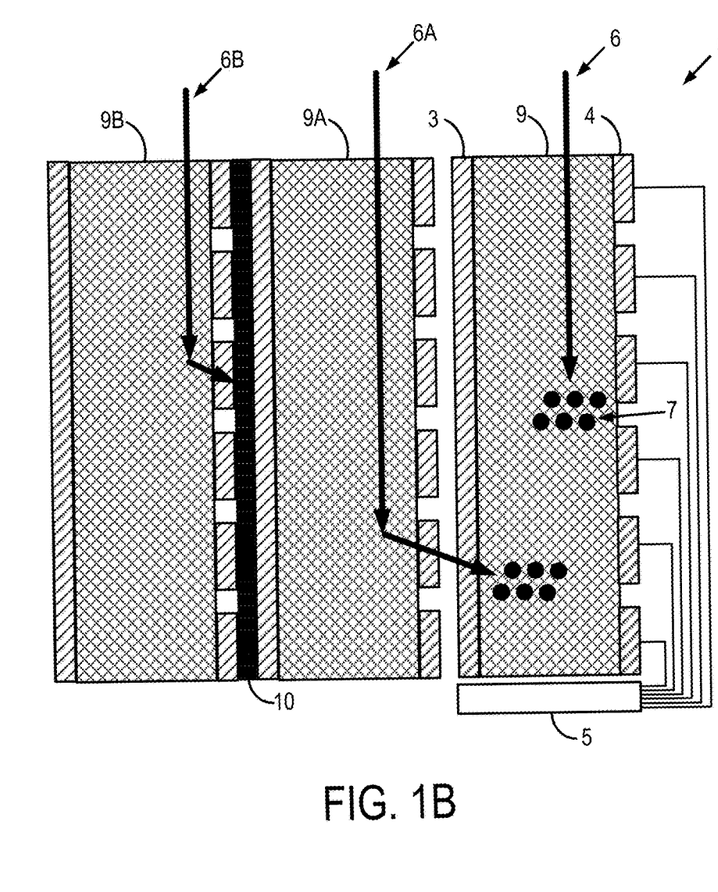
FIG. 1B is a schematic diagram of another, traditional PC detector, arranged in an edge-on orientation.

As a function of these properties, the design of PCD detectors differs based on the semiconductor. FIG. 1A shows a traditional CdTe-based PCD and FIG. 1B shows a Si-based PCD. Referring to FIG. 1A, a CdTe-based detector 1, includes one or multiple layers of CdTe 2 arranged between electrodes 3, 4. A high potential difference is applied across the CdTe detector 2. One of the electrodes 4 is coupled to a readout chip S. Thus, as an x-ray 6 travels into the CdTe layer 2, electrons and holes 7 are generated that are then read out by the chip S. However, a significant fraction of electrons and holes 7 are lost before they are collected. That is, as illustrated in Table 1, the lifetimes of electrons and holes in Si are orders of magnitude longer than in CdTe. Compared with CdTe, electrons and holes can "live" longer in Si before impurities trap them. The long lifetime of Si enables a complete collection of those charges, whereas the short lifetime of CdTe means that a significant fraction of x-ray-induced charges are lost before they are collected by the readout electronics, which unfortunately degrades both non-spectral and spectral CT imaging performance.

In addition to the longer lifetime of electrons and holes in Si, the abundance and mature manufacturing technologies of Si have made high-purity Si readily available at a very-low cost. However, despite its advantageous semiconductive properties, Si has a seemingly disadvantageous feature: its low atomic number (Z=14). Because the probability of photoelectric x-ray absorption is approximately proportional to $Z^3$ to $Z^4$, the x-ray attenuation coefficients of CdTe or $Gd_2O_2S$ used in other CT detectors are orders of magnitude higher than that of Si.

To overcome the low-absorption challenge of Si, some have designed an edge-on Si-based detector. As illustrated in FIG. 1B, an Si-based detector 8 can be formed as an edge-on PCD, where a layer of Si 9 is rotated in a relative thickness compared to the layer of CdTe 2 of FIG. 1A. This edge-on geometry allows the effective depth of the Si PCD to be determined by the length (L) of each Si wafer instead of its thickness (t). Since L can be centimeters-long, the total probability of x-ray interaction within the Si sensor can be drastically increased. Meanwhile, since the major physical mechanism that contributes to x-ray interactions in Si is scattering (Compton and Rayleigh) at energies higher than 50 keV, only a small fraction of the input photons can be entirely absorbed via the photoelectric effect (PE) at the initial interaction site. The rest of the x-rays are scattered away, carrying away the majority or even all of the energy. Note that using the edge-on geometry to replace the face-on geometry only increases the total probability of initial interaction. However, it does not reduce the probability of scattering, which is entirely determined by Z and x-ray energy.

Unfortunately, Si-based detectors have a further drawback. The major physical mechanism that contributes to x-ray interactions in Si is Compton scattering, can mean that only a fraction of the input x-ray energy is properly deposited at the initial interaction location in the detector. For example, as illustrated by x-ray 6A, when Compton scattering occurs, the scattered x-ray carries away the majority or even all of the input energy and eventually deposits the energy at another spatial location, which can be an adjacent or remote Si detector elements 9A to receive x-ray 6A, which, as a result of Compton scattering deposits energy in the other Si layer 9. This degrades both spatial resolution and energy resolution of the detector 8. Notably, using the edge-on geometry of the Si-based detector to replace the face-on geometry common to the CdTe-based detector 1 only increases the total probability of X-ray interaction. It does not lower the probability of scatter because it is determined by the Z of Si.

To control the scatter problem in Si-based PCDs 8, some have inserted metallic spacers 10 between different rows of Si 9A and 9B. As a result, x-rays 6B can be scattered in S-layer 9B, but it is stopped in the spacer 10 without introducing inter-detector row crosstalk. However, this setup is detrimental to the radiation dose efficiency and image quality of CT systems. For example, 60% of the received x-rays can be absorbed in the spacer 10 instead of the Si sensor due to scattering within the detector (note that this is different from the patient-induced scatter).

In stark contrast, for face-on PCDs with CdTe 1, the photoelectric effect dominates and scatterings are negligible at typical x-ray energy levels in medical CT. Thus, no spacer is present in CdTe-based PCDs and the majority of the input x-rays can be absorbed by the CdTe sensor via the photoelectric effect. No matter whether a CT system uses a conventional detector or a PCD, the image noise is inversely proportional to the x-ray absorption efficiency. Therefore, the edge-on Si-PCDs with spacers 10 introduce a severe efficiency penalty that may have been overlooked by those who mainly focus on the energy resolution and cost benefits of Si.

Thus, it would be desirable to have systems and methods for improved PCDs for CT imaging.

SUMMARY

The present disclosure overcomes the aforementioned drawbacks by providing systems and methods for manufacture for a hybrid detector. The hybrid detector is able to generate photon-counting data and accurately detect scatter events as energy-integrating data. In one non-limiting configuration, no spacers are included in the detector array. Between semiconductor layers, a scintillator is included that is configured to detect scattered x-rays. In this system, all or almost all x-rays that reach the photon-counting detector system can be collected to thereby have the total radiation dose efficiency that is boosted, for example by a factor of at least two, compared to traditional Si-based PCDs or Si-based PCDs with spacers. Information deposited by the scattered x-rays can be utilized jointly with information recorded by the photon-counting detector for a more accurate estimation of the input x-rays' energies, elevating the energy resolution of the PCCT system and thus the spectral imaging performance. The scintillator can be a high-Z scintillator, such as $Gd_2O_2S$ (Gadox) or any other scintillator. A light detecting element or sensor can be coupled to the scintillator to acquire information carried by scattered x-rays.

In accordance with one aspect of the disclosure, a computed tomography (CT) medical imaging system is provided that includes an x-ray source configured to deliver x-rays to an object as the x-ray source is rotated about the object and a hybrid detector. The hybrid detector includes a semiconductor detector arranged to generate photon-counting CT data upon receiving x-rays and a scintillator detector arranged proximate to the semiconductor detector to receive scattered x-rays and generate energy-integrating CT data upon receiving the scattered x-rays.

In accordance with another aspect of the disclosure, a hybrid detector for a computed tomography (CT) system is provided that include a semiconductor detector arranged to generate photon-counting CT data upon receiving x-rays and a scintillator detector arranged proximate to the semiconductor detector to receive scattered x-rays and generate energy-integrating CT data upon receiving the scattered x-rays.

In accordance with one other aspect of the disclosure, a detector array for a computed tomography (CT) system is provided that includes a plurality of photon-counting detector elements configured to receive x-rays delivered to an object as an x-ray source is rotated about the object and, in response to receiving x-rays, generate photon-counting CT data. The detector array also includes a plurality of energy-integrating detector elements arranged to receive x-rays scattered within the plurality of photon-counting detector elements and, in response to receiving x-rays scattered within the plurality of photon-counting detector elements, generate energy-integrating CT data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 2A:
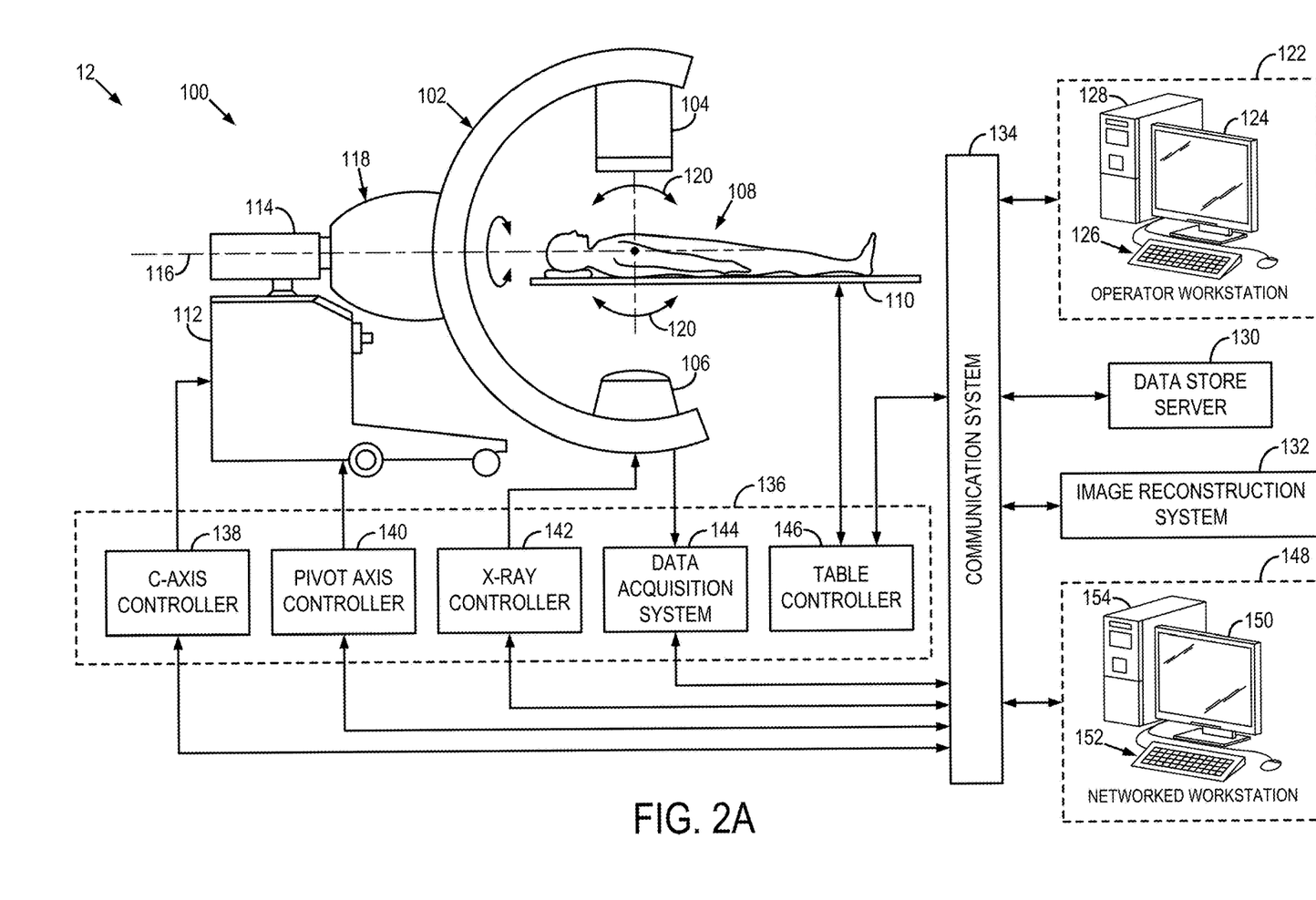
FIG. 2A is a schematic diagram of a C-arm x-ray computed tomography (CT) imaging system configured in accordance with the present disclosure.
Figure 2B:
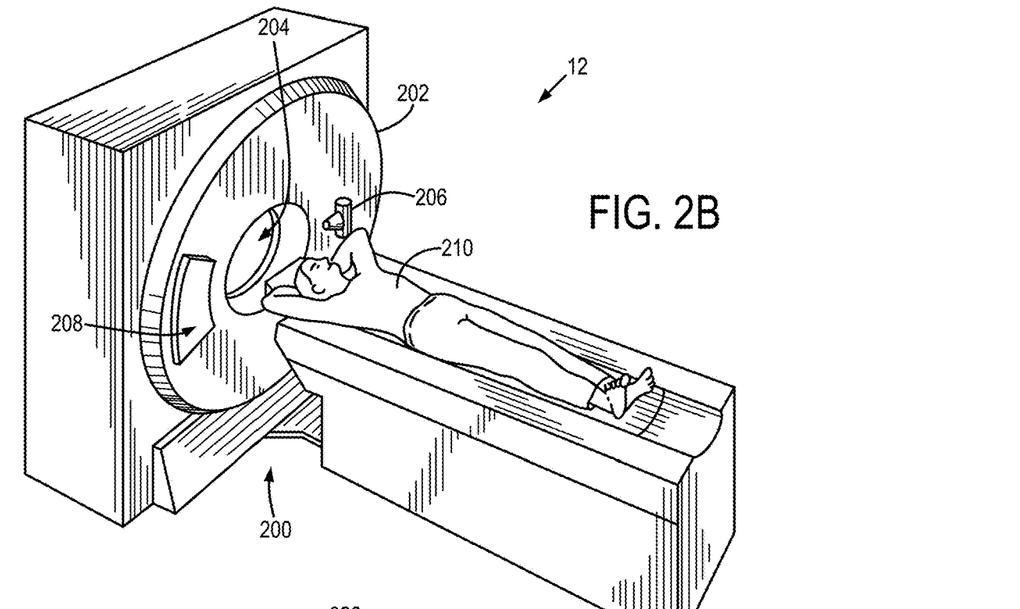
FIG. 2B is a perspective view of an example of an x-ray computed tomography (CT) system.

Referring to FIG. 2A, one, non-limiting example of the imaging system 12 that may be configured in accordance with systems and methods provided in the present disclosure is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 for use with the systems and methods of the present disclosure.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which will be described below.

Together, the x-ray detector elements in the one or more x-ray detectors housed in the x-ray detector array assembly 106 sense the projected x-rays that pass through a subject 108. Each x-ray detector element produces a signal that may represent the intensity of an impinging x-ray beam (in the case of a scintillator) or the specific energy or number of x-rays (in the case of an PCD, which may also be referred to as an energy discriminating detector) and, thus, the attenuation of the x-ray beam as it passes through the subject 108. In some configurations, each x-ray detector element is capable of counting the number of x-ray photons that impinge upon the detector and determine the energy (via energy integration) of scattered x-rays.

During a scan to acquire x-ray projection data, the gantry 102 and the components mounted thereon rotate about an isocenter of the C-arm x-ray imaging system 100. The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data are communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122 or on a mobile system or in the cloud. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Figure 2C:
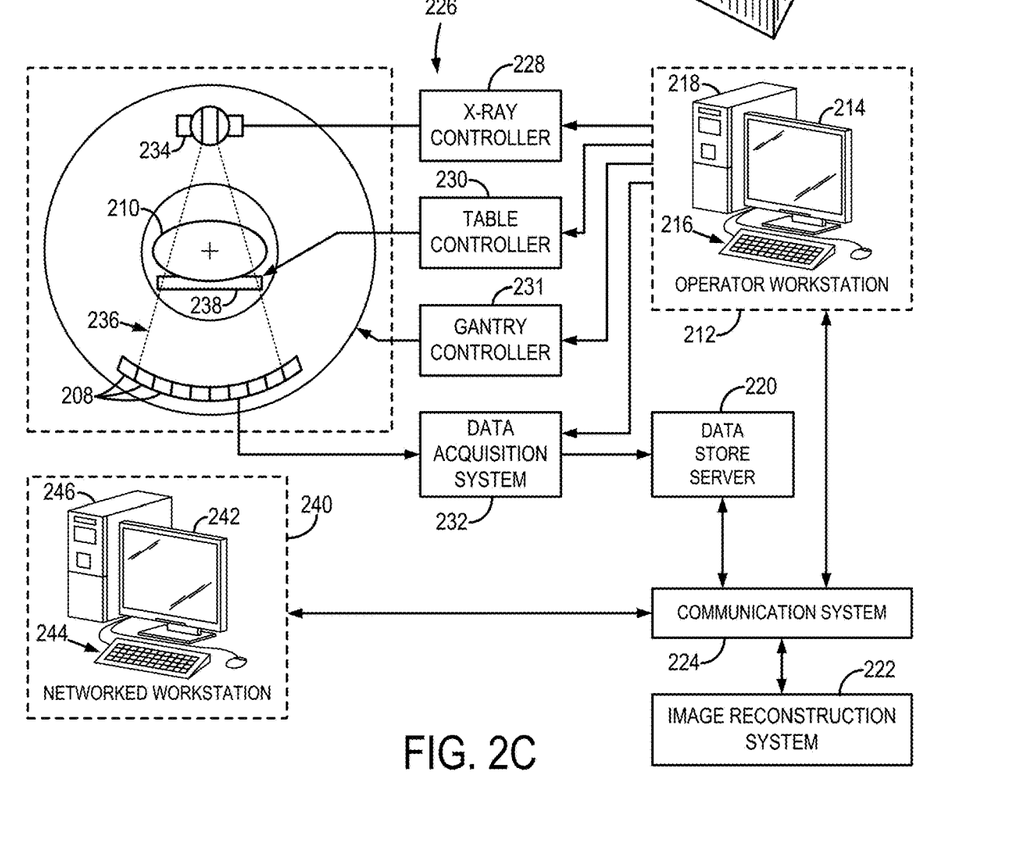
FIG. 2C is a block diagram of CT system, such as illustrated in FIG. 2B.

Similarly, referring to FIGS. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data are communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

As explained above, a substantial limitation with the existing Si-based PCD technology is that the majority of scattered x-rays are absorbed in the metallic spacers and, thus, information carried by those scattered x-rays gets entirely wasted. However, without the absorbing spacers, scattered x-rays can travel several centimeters in the Si to generate wrong counts at a remote pixel location.

The present disclosure provides a new Si-based PCD architecture that overcomes the drawbacks of those systems and is readily deployable to CT systems, such as described above with respect to FIGS. 2A-2C. In particular, as will be described, a hybrid photon counting/scintillator detector design is provided that provides increased efficiency in utilization of the input x-ray photons and increased accuracy in the reconstruction of input photon energies for spectral CT imaging applications, while using readily available photon counting and scintillator materials. Thus, a cost-effective, high-efficiency hybrid CT detector is provided. The hybrid detector may combine a PC detector elements with energy integrating detector elements, where the primary detector elements are PC detector elements and the energy-integrating detector elements are designed to capture scatter. Furthermore, systems and methods are provided to manufacture the hybrid detector and reconstruct images form the hybrid detector of the present disclosure.

Figure 3A:
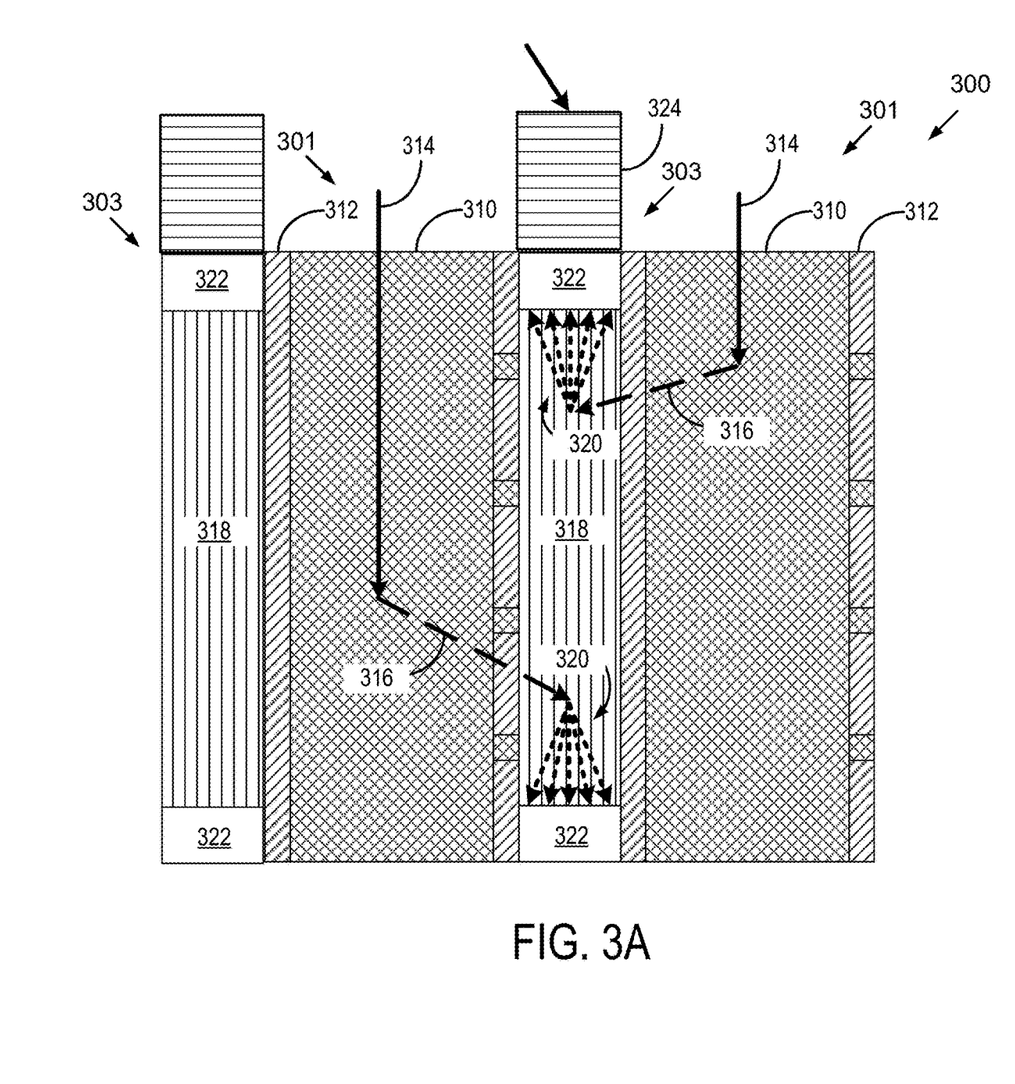
FIG. 3A is an example of a detector configuration in accordance with the present disclosure.

Referring to FIG. 3A, one configuration of a hybrid detector 300 forms a detector array. In particular, the array includes a plurality of photon-counting detectors (or semiconductor detector) 301 and a plurality of an energy-integrating detectors (or scintillator detector) 303. Each of the plurality of photon-counting detectors 301 includes a photon-counting semiconductor layer 310. As illustrated, the photon-counting semiconductor layer 310 may be arranged in an edge-on orientation. However, an edge-on orientation is not required. For example, a face-on orientation may be used. The semiconductor layer 310 may be Si or may include other desired materials. Electrode pads 312 are arranged about the photon-counting semiconductor layer 310.

The hybrid detector 300 does not include any spacer or material configured to block, redirect, or absorb scattered x-rays. In particular, as described above, as x-rays 314 move into the photon-counting semiconductor layer 310, some x-rays may scatter 316 and leave the photon-counting semiconductor layer 310. Arranged between adjacent photon-counting semiconductor layers 310 and associated electrode pads 312 is a respective one(s) of the plurality of an energy-integrating detectors 303. The energy-integrating detectors 303 include a scintillator 318. In this way, scattered x-rays 316 entering the scintillator 318 generate visible light 320 that is then detected by a light detecting device 322, such as a photodiode. Thus, the scintillator 318 and light detecting device 322, to together, form a second detector that is configured to acquire data form scattered x-rays, as opposed to wasting the information associated with scattered x-rays, such as is commonly done in many traditional PC detectors, such as described above. In addition, an anti-scatter grid 324 may optionally be utilized with this configuration. For example, anti-scatter grid 324 may be arranged over the scintillator 318 and serve to block, for example, x-rays scattered by the patient.

The scintillator 318 may be a high-Z scintillator, for example, it may include $Gd_2O_2S$. The light detecting device 322 may be a light sensor arranged to salvage information carried by scattered x-rays. As illustrated in FIG. 3A, the light detecting device 322 may be arranged on opposing sides of the scintillator 318, but may additionally or alternatively be arranged in other locations, as will be described. By arranging the light detecting device 322 at the upper and lower extents of the scintillator 318, electrical connections are readily available and serviceable.

The hybrid detector 300 provides substantial benefits not available in current PC detectors. For example, almost all x-rays that reach the hybrid detector 300 can be collected (minus those purposefully rejected as patient scatter, such as using the anti-scatter grid 324). Therefore, the total radiation dose efficiency can be boosted by, for example, a factor of at least two over systems that use spacers, for example formed of tungsten, to reject Compton scattered x-rays. Also advantageously, information deposited by the scattered x-rays can be utilized jointly with information recorded by the photon counting semiconductor layer for a more accurate estimation of the total x-rays input energies, elevating the energy resolution of the PCCT system and, thus, the spectral imaging performance.

Figure 3B:
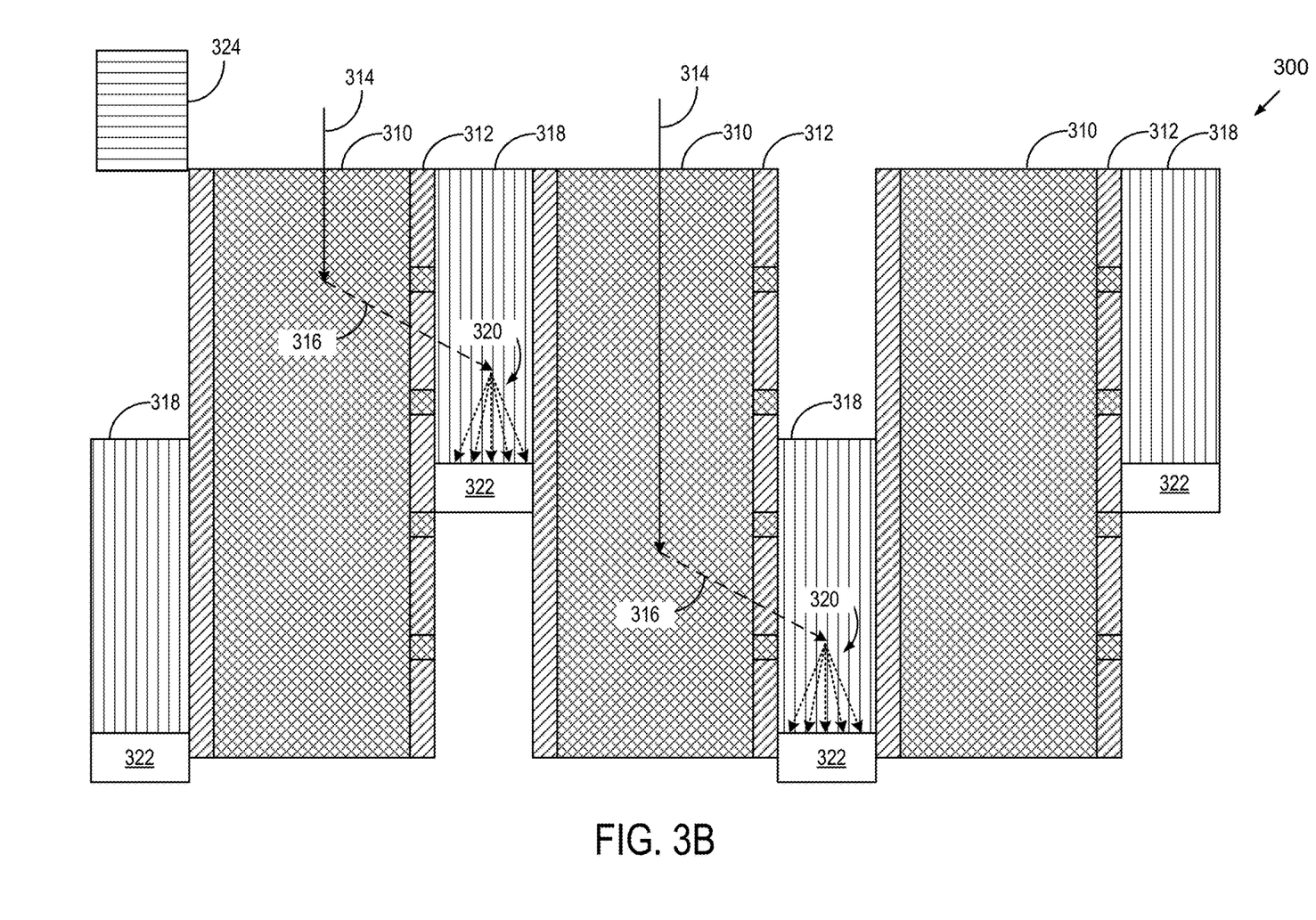
FIG. 3B is a further example of a detector configuration in accordance with the present disclosure.

As a further variation on the configuration illustrated in FIG. 3A and referring to FIG. 3B, the hybrid detector 300 is illustrated with the scintillator 318 and light detecting device 322 arranged in pairs such that an "upper" scintillator 318 and light detecting device 322 are on one side of the semiconductor layer 310 and a "lower" scintillator 318 and light detecting device 322 are arranged on the other side of the semiconductor layer 310. In this configuration of the hybrid detector of FIG. 3B, each scintillator 318 is only half of the length of the semiconductor layer 310 and the light detecting device 322 is attached to the bottom of the scintillator 310 to increase the light collection efficiency over the use of single light detecting device 322 arranged at the bottom of a scintillator 318 matched in length to the semiconductor layer 310. In this configuration, the spaces without the scintillator 318 may be used for wiring or other electronics, and may include shielding to stop scatter across multiple detector columns.

Figure 3C:
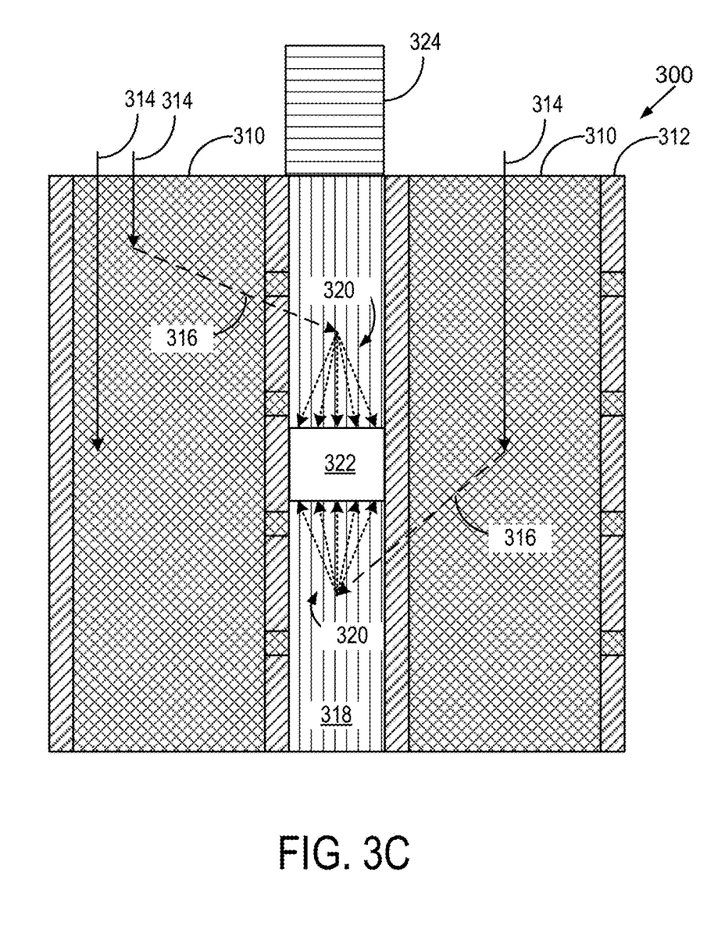
FIG. 3C is an example of a detector configuration in accordance with the present disclosure.

Referring to FIG. 3C, instead of "upper" and "lower" scintillators 318 on opposite sides of the semiconductor layer 310, both the upper and lower scintillator 318 may be arranged on the same side with the light detecting device 322 arranged therebetween. In this way, the light collection efficiency remains high, while maintaining a high percentage of collection of scattered signal.

Figure 3D:
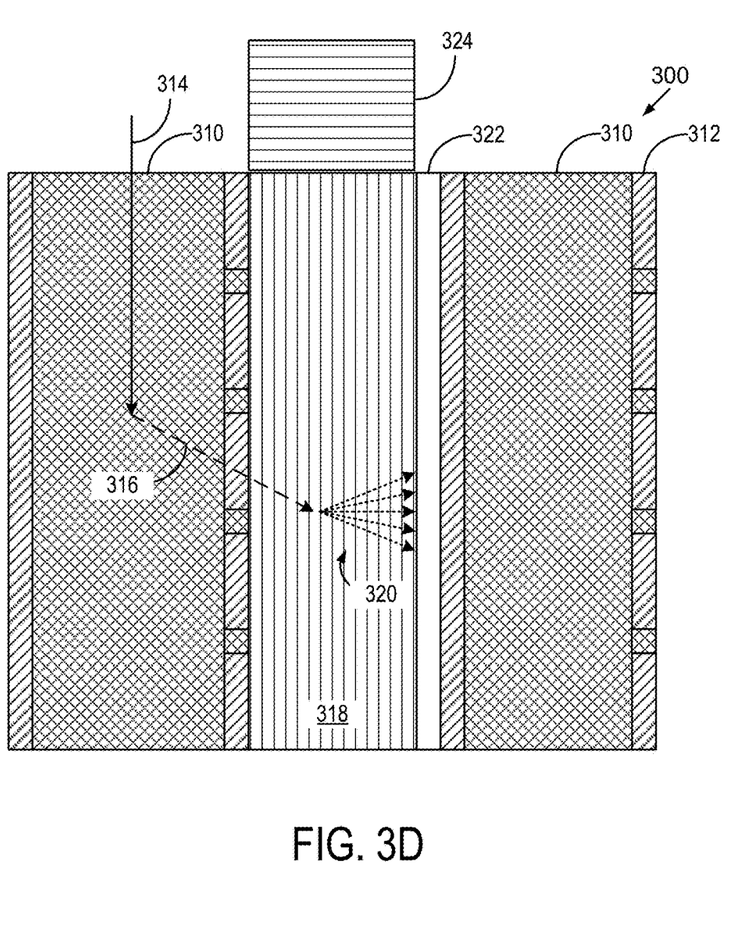
FIG. 3D is a further example of a detector configuration in accordance with the present disclosure.

Referring to FIG. 3D, the light detecting device 322 may be placed on the side of the scintillator 318 and run the extent of both the scintillator 318 and the semiconductor layer 310. Again, light collection efficiency remains high, while maintaining a high percentage of collection of scattered signal. As described above, the light detecting device 322 may be arranged above, below, within, or alongside of the scintillator 318.

Thus, the present disclosure provides multiple ways to construct the hybrid detector 300. Information collected at the semiconductor layer and scintillators can be jointly utilized to generate CT images. Radiation physics has determined that the majority of the scattered x-rays collected at the scintillator sensors are of higher energies. In contrast, the outputs of the semiconductor layers, such as Si sensors, are dominated by low energy x-rays. Therefore, the outputs of the scintillator sensors can provide an additional energy channel to supplement the energy bin data of a semiconductor layer of a PCD. This can benefit the generation of spectral CT images, such as iodine material image, since a more-complete recording of the x-ray energy is provided by the hybrid detector.

Deep neural networks can be used to directly accomplish the inference of both spectral and non-spectral CT images from the readouts of the hybrid detectors. The inputs of this network are the signals of the scintillator and counts of different energy bins from the PCD. The outputs of the network are the total attenuation projection image plus the material basis projection images, from which virtual monoenergetic images and other spectral CT images can be reconstructed.

EXAMPLES

Both physical experiments and Monte-Carlo simulations were performed using the above-described systems and methods. Results of the physical experiments were used to validate the Monte-Carlo method. Once validated, Monte-Carlo simulations were used with great flexibility (e.g., with different Si PCD configurations).

A benchtop system with the geometry and beam quality of clinical CT was used. Polychromatic x-rays were produced by rotating tungsten (W) anode tube and were collimated by two lead pinholes to become a sub-mm pencil beam. Si wafers with a thickness (t) of 500 μm were diced to have a length (L) of 4 cm and were placed edge-on to the pencil beam. A high-sensitivity CdTe PCD was placed to the side of the Si wafers to experimentally measure the number of x-ray photons side-scattered by the Si. With a two mm-thick CdTe sensor layer, anti-charge corrections, negligible pulse pileups, and almost complete rejection of electronic noise, the efficiency of the CdTe PCD in detecting scattered photons below 80 keV was almost 100%. Measurements were performed at seven tube potentials from 60-120 kV. For each spectrum, the CdTe PCD was placed face-on to the pencil beam both with and without the Si to measure the input photon number and the number of primary photons absorbed in Si.

Also, the Geant4 Application for Tomographic Emission (GATE) toolkit was used to perform the Monte-Carlo simulation. The thickness of the W septa was adjusted from 0 to 250 μm; the x-ray tube potential was changed from 60 to 140 kV. The assumed electronic noise level, $\sigma_e$, of the Si PCD system was 1.5 keV. For each system condition, 1,000,000 x-ray photon events were simulated. The type and energy deposition for each interaction with the Si PCD was traced and recorded for each photon. Results gave the upper limits of the edge-on PCD performance because the electron and hole transports, which can introduce additional noises and information loss, were not considered in the simulation.

Side-scattered x-ray photons (by the Si PCD surrogate) were experimentally captured by the CdTe PCD. The x-ray Bragg diffraction generated a horizontal streak pattern in the image by the Si crystal lattice. Using the measured scatter and primary photon numbers, the percentage of input x-rays that were directly absorbed in the Si was calculated. The Monte-Carlo results agreed reasonably well with the experimental data. The slight discrepancy was due to the decreased x-ray absorption efficiency of the CdTe PCD at higher energies.

Figure 4A:
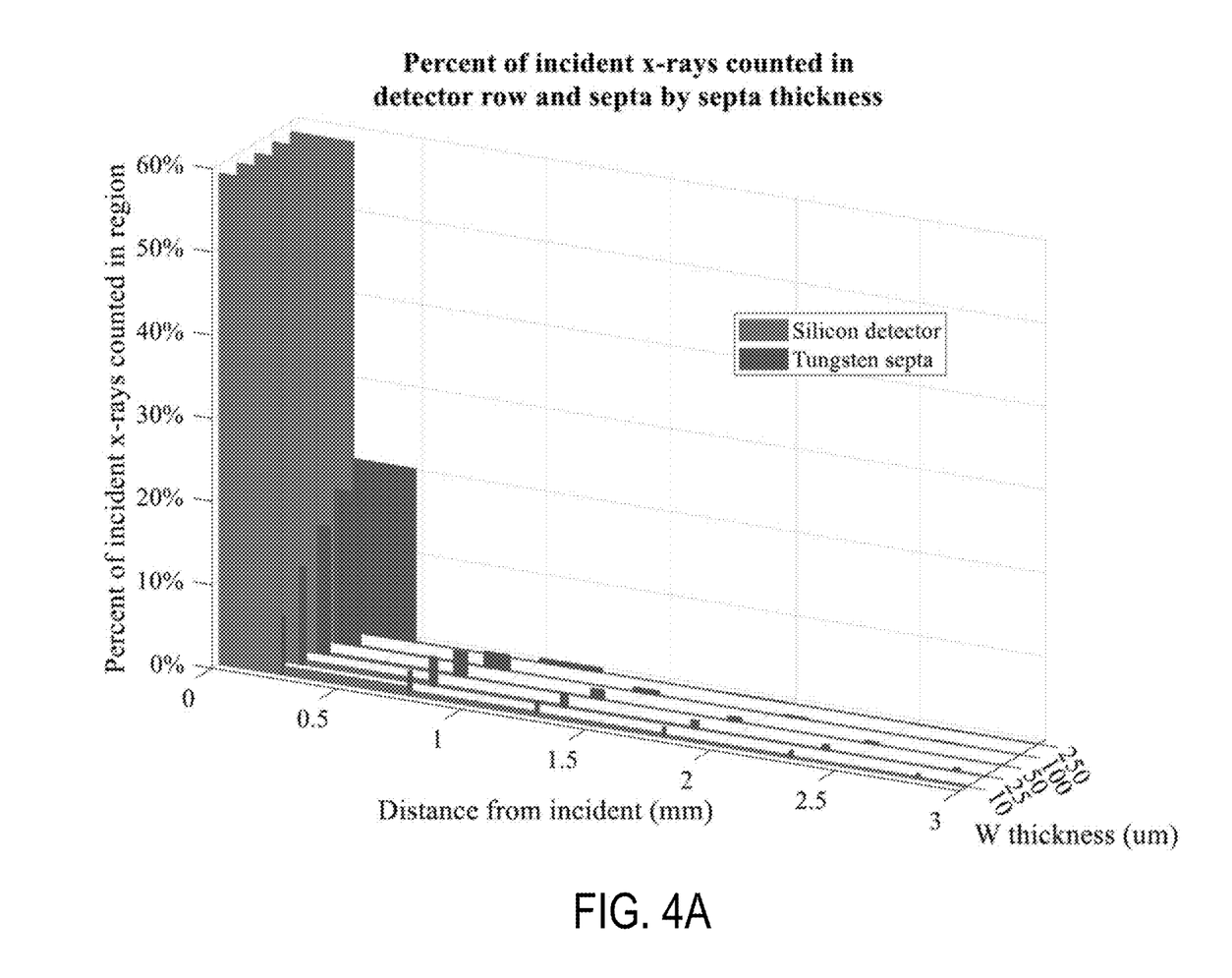
FIG. 4A is a graph showing percentages of incident x-rays absorbed in each detector row or W septa.
Figure 4B:
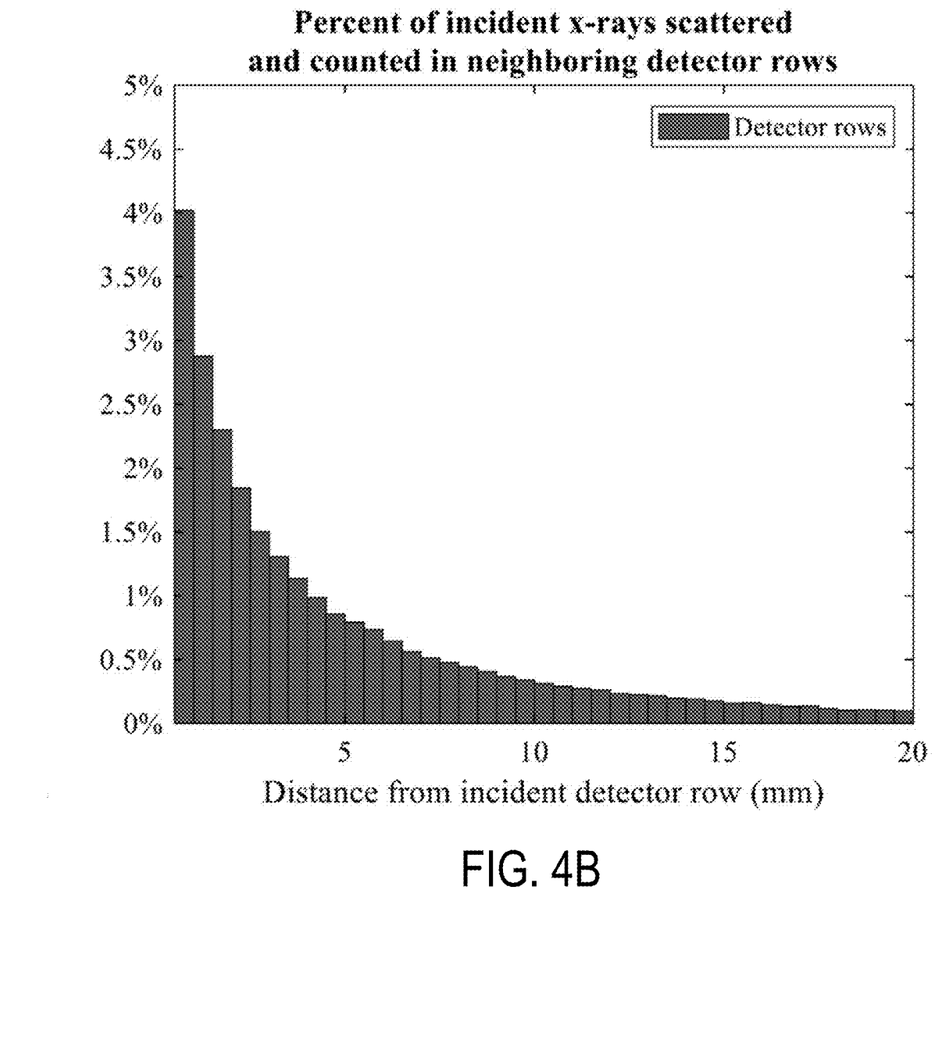
FIG. 4B is a graph showing percentages of scattered x-rays absorbed in each detector row without septa. kV=120.

After its validation, Monte-Carlo simulations were used to evaluate the destinations of incident x-rays as a function of W septa thickness. As shown in FIG. 4A, the total percent absorption of incident x-rays has a weak dependence on the W septa thickness. The overall absorption efficiency is about 52% at 120 kV with a low energy threshold of 15 keV. When a scattered x-ray goes through one W septa, it will eventually be absorbed in another W septa due to orders of magnitude-higher W absorption coefficient than Si. When the W septa were removed, the overall x-ray absorption efficiency was improved to 75% at 120 kV with a threshold of 15 keV. Meanwhile, as shown in FIG. 4B, scattered x-rays can travel multiple detector rows before re-absorbing.

Thus, a large percentage of input x-rays can be scattered sideways within Si PCDs, which can lead to a severe resolution loss along the slice direction. For scatter control, W septa were introduced between detector rows, but their presence makes the majority of the input x-rays eventually end in W instead of Si. To meet the clinical and regulatory requirements about the quantum efficiency of CT detectors, information carried by those side-scattered photons needs to be harvested and utilized in the image formation. A variety of strategies and physical configurations were reviewed experimentally.

Figure 5:
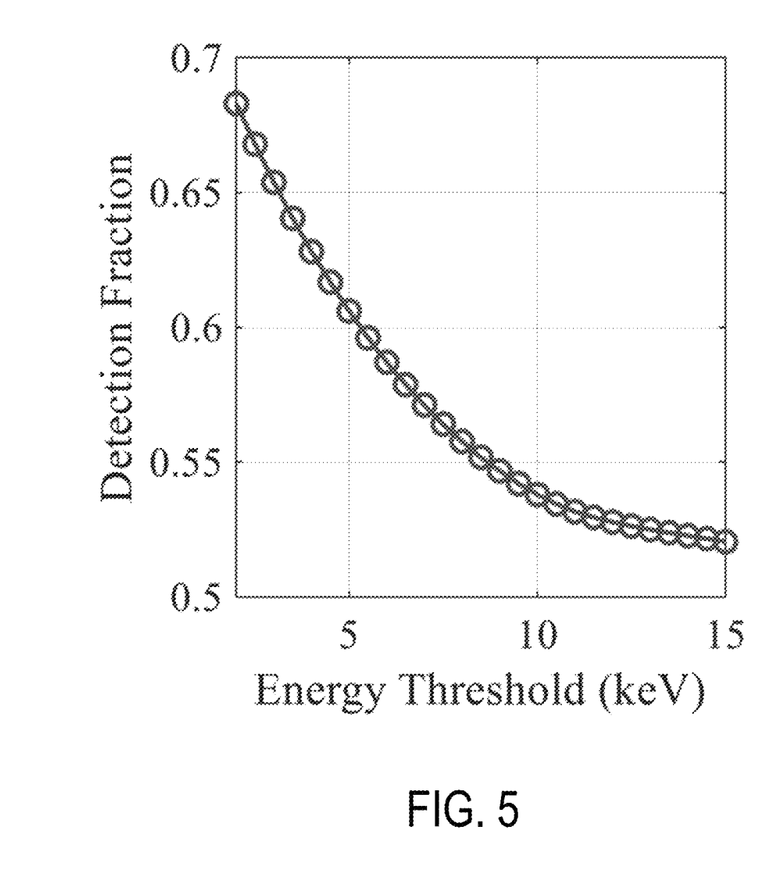
FIG. 5 is a graph showing the ratio between detected counts and the input photon number plotted as a function of the lowest energy threshold.

In a first strategy, the design was created to decrease the PCD energy threshold to allow more Compton events to trigger digital counts. For each Compton scattering, the energy transferred to the Si is given by $$\Delta E = E - \frac{E}{1 + E/m_e c^2 (1 - \cos \theta)},$$

where E is the input photon energy and θ is the scattering angle. Depending on θ, a Compton scattering of a 60 keV photon can transfer between 0 keV (θ=0) and 11 keV (θ=180) of its energy to Si. If the lowest energy threshold of the PCD is reduced from 20 keV to 3 keV, as shown in FIG. 5, the ratio between the detected counts and the number of x-ray photons from a 120-kV beam increases from 0.52 to 0.65. However, since ΔE is significantly smaller than the input photon energy E, algorithms are needed to deduce E from ΔE for spectral CT applications.

Figure 6:
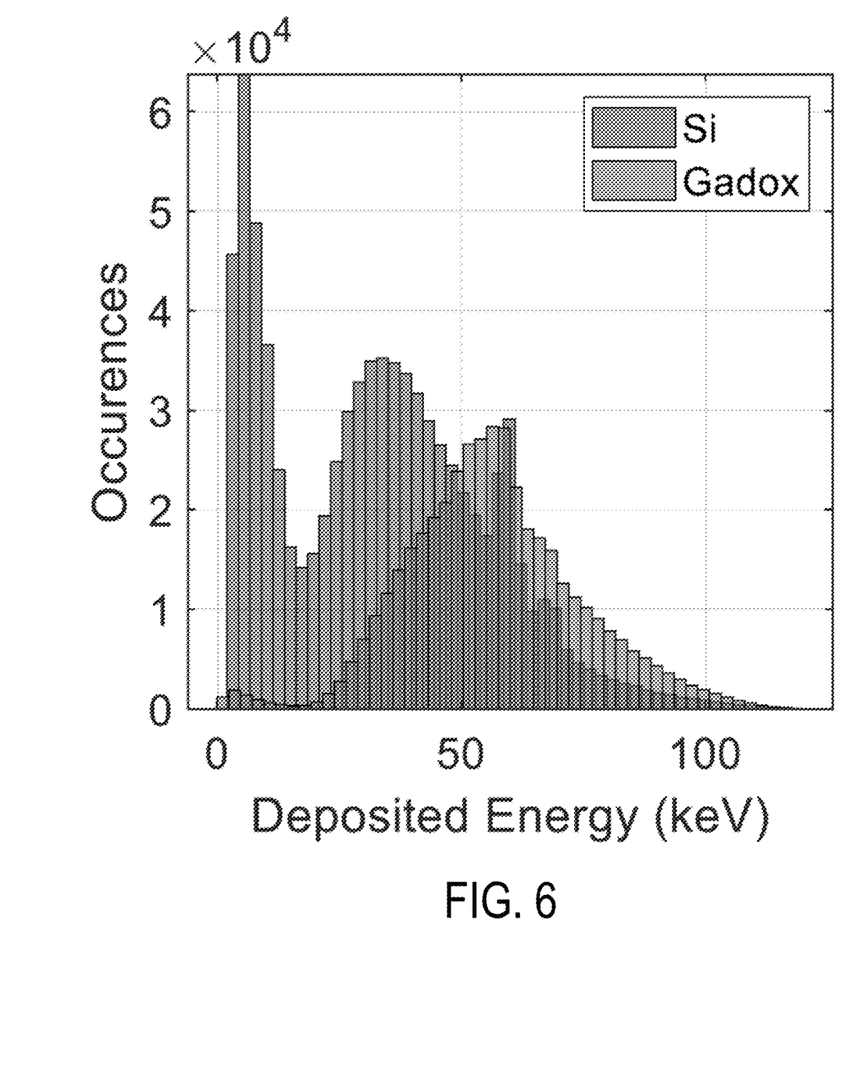
FIG. 6 is a graph showing the distribution of x-ray energy depositions in the Si and scintillator (Gadox) layers. The number of input x-ray photons is 1×106. Thickness of Si=0.5 mm; thickness of Gadox=0.25 mm. kV=120. PE: photoelectric effect.

In a second strategy, the hybrid detector design of the present disclosure was considered. In this case, the configuration of 3A was considered), the W septa was replaced by high-Z scintillating materials, such as Gadox, coupled with light sensors to salvage information carried by scattered x-rays. This hybrid detector design offers multiple benefits. First, almost all input x-rays can be collected, and therefore the total radiation dose efficiency can be boosted by a factor of at least two. Also, information deposited by the scattered x-rays can be utilized jointly with information recorded by the Si sensors for a more accurate estimation of the input photon energies. As shown in FIG. 6, among all x-ray interactions in the hybrid detector, 70% occur in the Si while the remaining 30% occur in Gadox. However, most of the interactions in Gadox are photoelectric and, thus, deposit much higher energy per interaction. Even with a light correction efficiency of only 1 percent, the total energy collected by Gadox is still an order of magnitude higher than that in Si. Thus, the designs of the present disclosure generate substantial additional image signals from the Gadox detector rows to supplement the readout of Si detector rows.

Therefore, a hybrid semiconductor/scintillator or photon-counting/energy-integrating detector design is provided that is substantially more efficient than PCD with respect to utilization of the input x-ray photons. The hybrid detectors provided herein can use readily available materials, such as Si for the semiconductor layer and traditional scintillator materials, to be highly cost efficient. Also, the hybrid detector yields a more accurate reconstruction of input photon energies for spectral CT imaging applications than PCDs can deliver.

In edge-on irradiated Si PCD-CTs, a significant fraction of input x-rays is scattered sideways. When inter-row W septa are incorporated for controlling the spatial spreading of the side-scattered photons, most of the input x-ray energy is deposited in W. To help harvest the energy information of the side-scattered photons, multiple strategies and configurations are provided herein. In some designs can seek to decrease the lowest energy threshold of the PCD to allow more Compton events to trigger digital counts. Other designs insert scintillator detector rows between Si detector rows to record the energy of scattered x-rays. Monte-Carlo simulations show that the energy information recorded by the scintillator rows is complementary to Si detector rows and can efficiently utilize x-ray information.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A computed tomography (CT) medical imaging system comprising:
   an x-ray source configured to deliver x-rays to an object as the x-ray source is rotated about the object;
   a hybrid detector comprising:
     a semiconductor detector arranged to generate photon-counting CT data upon receiving x-rays; and
     a scintillator detector arranged proximate to the semiconductor detector to receive x-rays scattered from within the semiconductor detector and generate energy-integrating CT data upon receiving the x-rays scattered from within the semiconductor detector; and
   a processor configured to use the energy-integrating CT data jointly with the photon-counting data to increase total radiation dose efficiency over the photon-counting data alone.

2. The system of claim 1, wherein the scintillator detector includes a scintillator and a light-detecting device.

3. The system of claim 2, wherein the light-detecting device includes a photodiode.

4. The system of claim 2, wherein the light-detecting device is arranged above, below, within, or alongside of the scintillator.

5. The system of claim 2, wherein the scintillator is divided into an upper scintillator arranged on one side of the semiconductor detector and a lower scintillator arranged on another side of the semiconductor detector.

6. The system of claim 1, wherein the semiconductor is arranged to receive x-rays in an edge-on orientation.

7. The system of claim 1, further comprising a plurality of scintillator detectors, each scintillator detector arranged between adjacent semiconductor detectors to form a detector array.

8. The system of claim 1, wherein the semiconductor detector includes silicon, CdTe, or CZT.

9. The system of claim 1, wherein the scintillator detector includes $Gd_2O_2S$.

10. The system of claim 1, further comprising a processor configured to receive the photon-counting CT data and the energy-integrating CT data and reconstruct an image of the object from the photon-counting CT data and the energy-integrating CT data.

11. The system of claim 1, further comprising an anti-scatter grid arranged to block x-rays from entering the scintillator detector from a location outside of the semiconductor detector.

12. A hybrid detector for a computed tomography (CT) system comprising:
    a semiconductor detector arranged to generate photon-counting CT data upon receiving x-rays; and
    a scintillator detector arranged proximate to the semiconductor detector to receive x-rays scattered from within the semiconductor detector and generate energy-integrating CT data upon receiving the x-rays scattered from within the semiconductor detector.

13. The system of claim 12, wherein the scintillator detector includes a scintillator and a photodiode.

14. The system of claim 13, wherein the light-detecting device is arranged above, below, within, or alongside of the scintillator.

15. The system of claim 13, wherein the scintillator is divided into an upper scintillator arranged on one side of the semiconductor detector and a lower scintillator arranged on another side of the semiconductor detector.

16. The system of claim 12, wherein the semiconductor is arranged to receive x-rays in an edge-on orientation.

17. The system of claim 12, further comprising a plurality of scintillator detectors, each scintillator detector arranged between adjacent semiconductor detectors to form a detector array.

18. The system of claim 12, wherein the semiconductor detector includes silicon or the scintillator detector includes $Gd_2O_2S$, CdTe, or CZT.

19. The system of claim 12, further comprising an anti-scatter grid arranged to block x-rays from entering the scintillator detector from a location outside of the semiconductor detector.

20. A detector array for a computed tomography (CT) system comprising:
    a plurality of photon-counting detector elements configured to receive x-rays delivered to an object as an x-ray source is rotated about the object and, in response to receiving x-rays, generate photon-counting CT data; and
    a plurality of energy-integrating detector elements arranged to receive x-rays scattered within the plurality of photon-counting detector elements and, in response to receiving x-rays scattered within the plurality of photon-counting detector elements, generate energy-integrating CT data.

21. The detector array of claim 20, wherein each of the plurality of photon-counting detector elements includes a semiconductor detector layer or each of the plurality of energy-integrating detector elements includes a scintillator or photodiode.

22. The detector array of claim 20, wherein each of the plurality of energy-integrating detector elements is arranged between adjacent ones of the plurality of photon-counting detector elements.

* * * * *